United States Patent [19]

Santangelo

[11] Patent Number: 5,067,477
[45] Date of Patent: Nov. 26, 1991

[54] LOW WEAR BEARING FOR A SURGICAL RETRACTOR

[75] Inventor: John Santangelo, East Freetown, Mass.

[73] Assignee: Codman & Shurtleff, Inc., Randolph, Mass.

[21] Appl. No.: 388,109

[22] Filed: Aug. 1, 1989

[51] Int. Cl.[5] .................................................. A61B 17/02
[52] U.S. Cl. .......................................... 128/20; 74/422
[58] Field of Search ............... 128/20, 17, 18; 74/422; 269/227, 202; 254/95-97, DIG. 6

[56] References Cited

U.S. PATENT DOCUMENTS

| | | | |
|---|---|---|---|
| 3,656,364 | 4/1972 | Cable et al. | 74/422 |
| 4,627,421 | 12/1986 | Symbas et al. | 128/20 |
| 4,702,230 | 10/1987 | Pelta | 128/20 |
| 4,726,356 | 2/1988 | Santilli | 128/20 |
| 4,747,394 | 5/1988 | Watanabe | 128/20 |

FOREIGN PATENT DOCUMENTS 1019217  1/1953  France ............................. 128/20

Primary Examiner—Edward M. Coven

[57] ABSTRACT

A low wear bearing system for a surgical retractor including usually four bearings recessed in the retractor housing, each bearing having a generally rectangular projection extending into a corresponding slot in the rack of the rack and pinion type retractor. There are two bearings on each side of the rack spaced longitudinally along the rack. The bearings provide an enlarged buffer area of contact between the rack and the housing to distribute the relatively high internal retraction forces that can be experienced during tissue retraction.

7 Claims, 2 Drawing Sheets

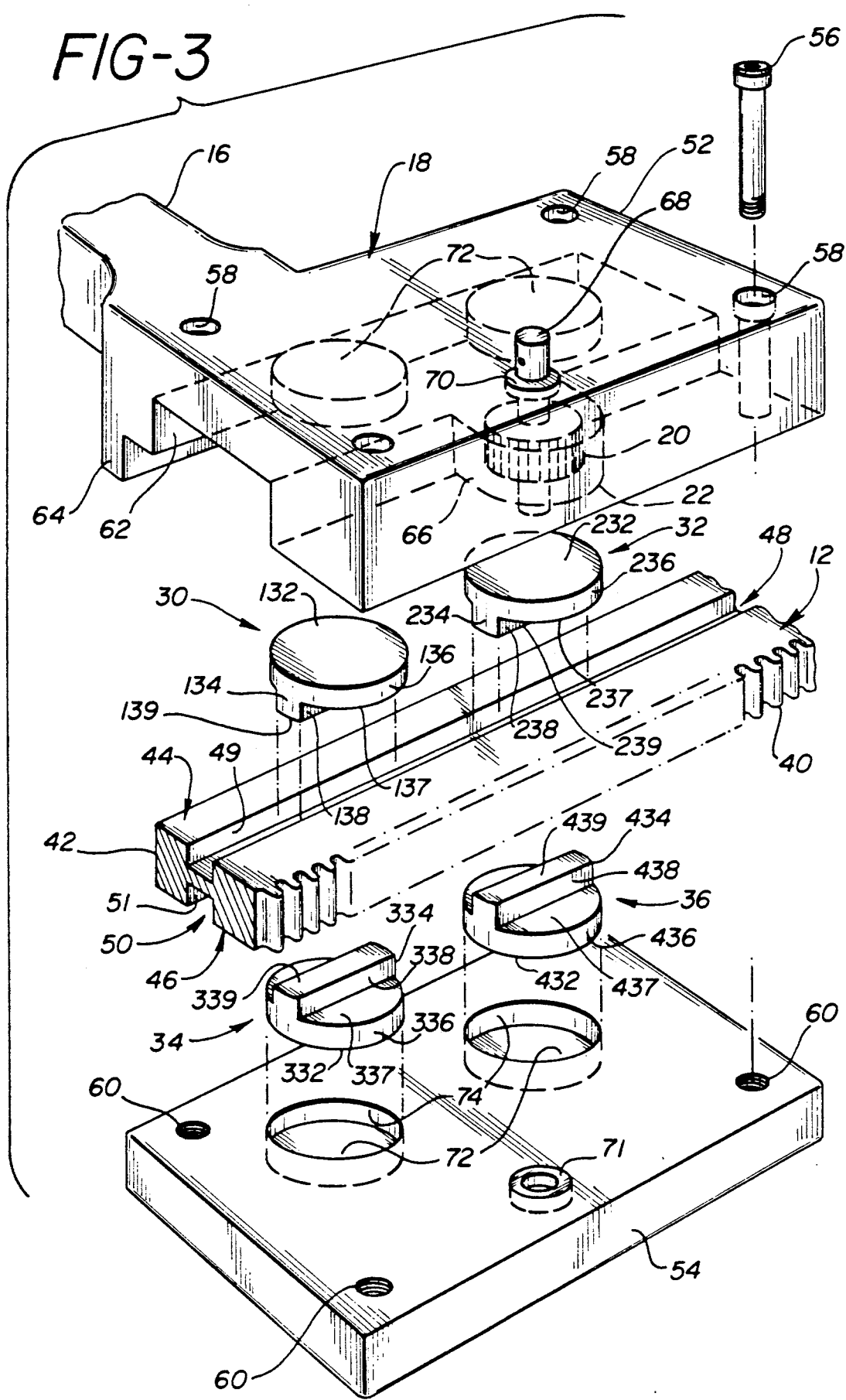

LOW WEAR BEARING FOR A SURGICAL RETRACTOR

The present invention relates to a low wear bearing system for a surgical retractor and more particularly bearings which reduce or eliminate undesirable kinds of metal-to-metal contact in a rack and pinion type retractor of the kind used commonly in abdominal, spinal or thoracic surgery.

BACKGROUND OF THE INVENTION

Rack and pinion type retractors are commonly used to hold a surgical incision open to provide access to the interior of the body. Retractor arms which can support various kinds of retractor blades are suspended over or rest on the patient. Generally, one arm is fixed and the other arm moves along a rack under the influence of a pinion driven by a rotatable handle. However, in certain retractors, both arms move with the rack. The handle is turned to operate a pinion against a rack and move one of the arms away from the other to open the wound under the influence of retractor blades which are inserted through the incision. Often large forces are experienced by the retractor. Since the retractor arms extend from the rack significant forces and moments can be developed at the point where the movable arm extends from the rack. The arm and the housing from which it extends tend to rotate about its supporting rack under the influence of the retraction forces. This rotation can cause undesirable metal-to-metal contact with significant force between various parts of the retractor which can make it difficult to operate the retractor and can subject the metal from which the retractor is made to high stresses which can cause undesirable wear to the parts.

It would be desirable to have a bearing system which could distribute the forces to which the retractor parts are subjected during use.

SUMMARY OF THE INVENTION

The present invention provides a low wear, high contact area bearing system to distribute the forces over a relatively large area and thus reduce the contact stresses experienced by the parts of the retractor during use.

At least two force distributing bearings are mounted within the housing portion of a conventional thoracic retractor. The force distributing means are spaced longitudinally along the rack of the rack and pinion type retractor. The rack and force distributing means interfit with one another with a slot on one element and a projection on the other. In the preferred embodiment, the rack has a longitudinal slot on at least one side for receiving the force distributing means projections between the rack and housing to provide a buffer against contact between the rack and the housing. The force distributing means are bearings with a cylindrical base and a generally rectangular projection extending from the base. The base fits into a recess in the housing from which one of the retractor arms is supported and the projection of the bearing fits into a slot in the rack. The contact area between the load bearing side surfaces of the bearing and the rack slot provides a relatively large area over which to distribute what can be relatively high internal reactions to the retraction forces transmitted to the housing.

Alternatively, each button may have more than one projection spaced side-by-side which fit into a corresponding number of slots in the confronting surface of the rack. In a further alternative embodiment, the rack may have a projection and the force distributing means may have slots.

The bearings are preferably made of a substantially nonabrading wearing material like plastic or bronze, however, a variety of other suitable materials can be used. Even the correct combination of hardened steel bearings and a steel rack can be used.

In the preferred embodiment there are two bearings on each side of the rack. In an alternative embodiment, there may be one bearing on each side of the rack spaced longitudinally along the rack. In a still further alternative embodiment both bearings may be on the same side of the rack also spaced longitudinally along the rack and the housing cover is made of a nonabrading wearing material.

In a still further modified embodiment, the exterior curvilinear surface of the bearing can be fluted, cogged or shaped and the recess in the retractor housing which receives the bearing will be similarly curved, fluted, cogged or shaped. The contact between the curved, fluted, cogged or shaped complimentary surfaces of the bearing and the recess provide substantial contact area over which to distribute the reaction forces.

These and other features of the present invention will be more readily appreciated from the detailed description of the preferred embodiment and the following drawings.

BRIEF DESCRIPTION OF THE DRAWINGS

FIG. 3 shows an exploded perspective view of the rack and pinion portion of the retractor with the housing portion of the movable arm.

DETAILED DESCRIPTION OF THE PREFERRED EMBODIMENT

Figure 1:
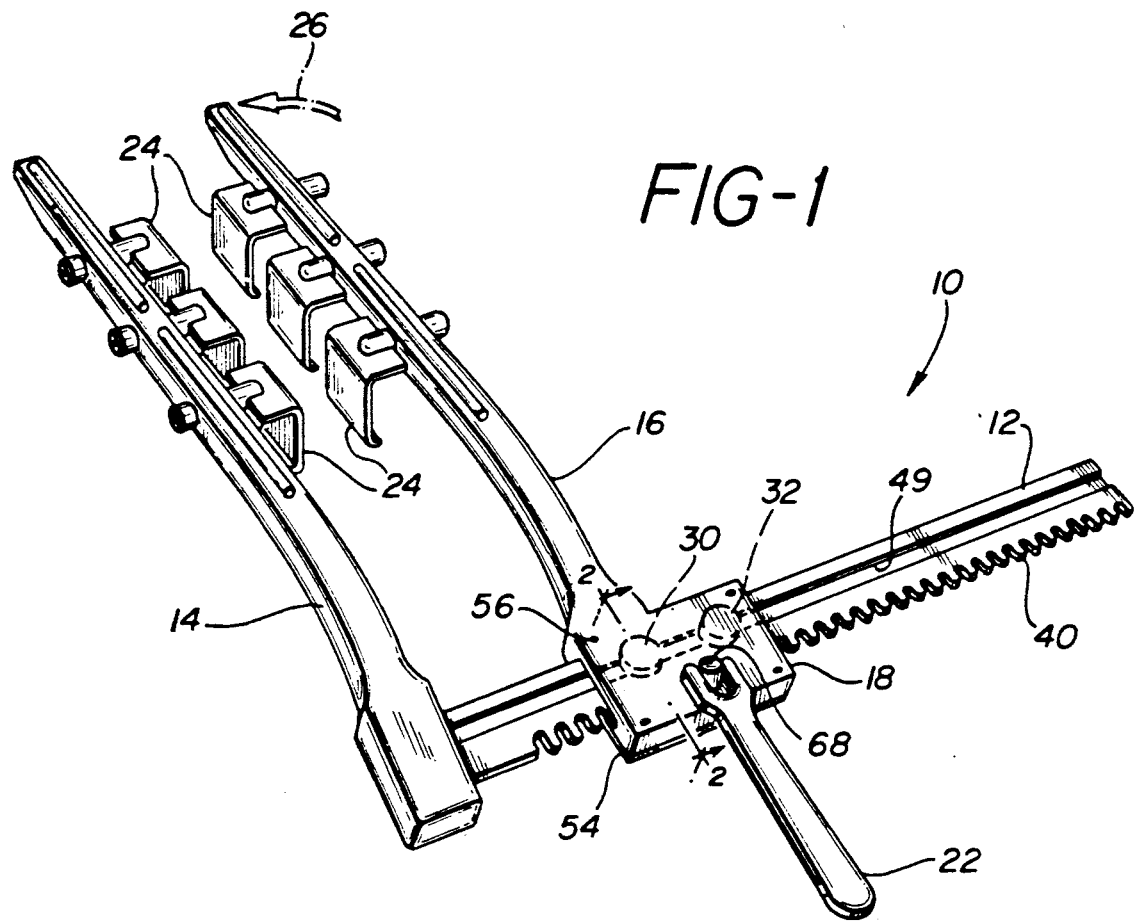
FIG. 1 shows a perspective view of a retractor of the present invention.

Referring now to FIG. 1, there is shown a retractor in which the low wear, high contact area bearings of the present invention can be employed. Retractor 10 includes a rack 12 from which a first arm 14 extends to one side. First arm 14 is fixed to rack 12 preferably at one end. A second arm 16 extends from a housing 18. Housing 18 surrounds rack 12 and also supports pinion 20 which can be rotated by means of handle 22 affixed to pinion 20. Retractor blades 24 of various sizes and shapes can be supported from first and second arms 14 and 16 over the patient. The entire retractor assembly can be supported from the operating table (not shown) or the assembly can rest directly on the patient's body. Blades 24 may be inserted into the wound to spread the tissue apart as second arm 16 is moved away from first arm 14 when handle 22 is rotated to cause pinion 20 and its associated housing 18 to travel along rack 12.

The force exerted on second arm 16 by the retracted tissue is indicated by arrow 26. One can appreciate that since retractor blades 24 are located along arms 14 and 16 a distance from the rack 12 even low tissue retraction forces create moments to rotate arm 16 and its corresponding housing 18 with respect to rack 12. Since rack 12 goes through housing 18, this rotation causes parts of rack 12 to directly contact parts of housing 18 with relatively high forces. If the contact area between housing 18 and rack 12 is small the stresses can be undesirably high. The low wear, high contact area bearings 30 and 32 of the present invention are shown in phantom in FIG. 1.

Referring now to FIG. 3 there is shown an exploded perspective view of the housing 18 together with a portion of second arm 16 and rack 12 with bearings 30, 32, 34 and 36 and their relationship to rack 12 and housing 18 clearly illustrated.

Rack 12 is an elongated piece of high strength metal of generally rectangular cross-section having the rack teeth 40 on one edge and a flat surface 42 on the other edge. The two remaining sides 44 and 46 of the generally rectangular rack 12 each have a slot 48 and 50 respectively extending longitudinally along the length of rack 12. The configuration of surface 42 is unimportant but can be any shape that conveniently permits sliding of rack 12 within housing 18 as will be explained below. Slots 48 and 50 are preferably aligned with one another but that is not necessary. Slot 48, for example, can be moved closer to surface 42 and slot 50 can be moved closer to teeth 40 or the other way around.

Second arm 16 extends from housing 18. In the preferred embodiment second arm 16 and housing 18 are fashioned from one piece of material, but that is not necessary as long as arm 16 is rigidly attached to housing 18. Arm 16 could be pivotably attached to housing 18.

Still referring to FIG. 3, it is shown that housing 18 can include two parts; i.e., a housing base 52 and a housing cover 54 which is attached to housing base 52 by means of bolts 56 extending through bores 58 in base 52 and into tapped holes 60 in housing cover 54. Housing base 52 includes a channel 62 sized to receive rack 12 with a loose fit on the confronting surfaces of channel 62 and rack 12.

A flange 64 projects from base 52. Housing cover 54 is affixed to housing base 52 to enclose channel 62 and hold rack 12 in place.

Figure 2:
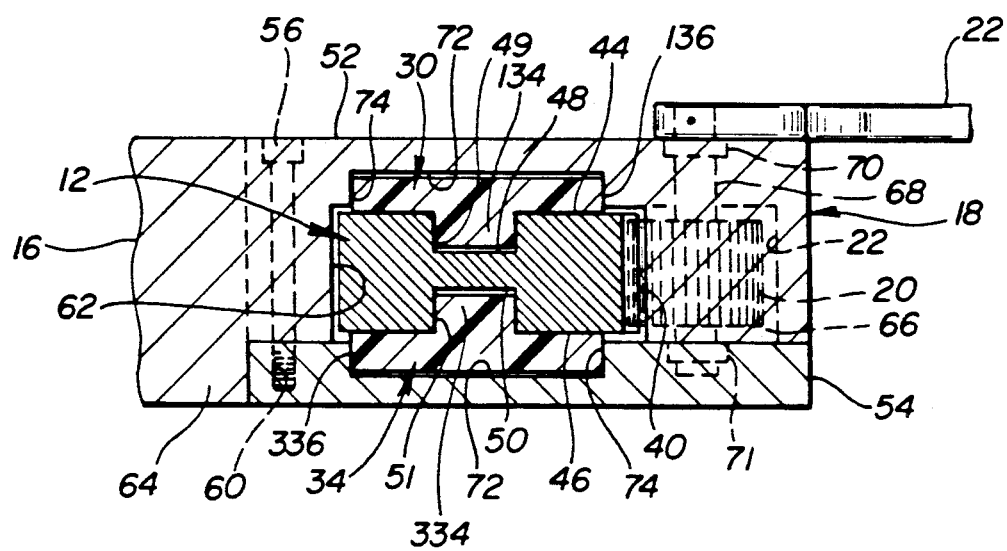
FIG. 2 shows a sectional view taken along lines 2—2 in FIG. 1 of a portion of the retractor in FIG. 1.

As can be seen best in FIG. 2, the thickness of flange 64 is equal to that of housing cover 54 to provide a smooth outer surface across flange 64 and the exterior of housing cover 54.

Also as shown in FIGS. 2 and 3, pinion 20 is supported within a recess 66 adjacent channel 62. Pinion shaft 68 is supported in housing base 52 by bushing 70 and in housing cover 54 by bushing 71. Pinion shaft 68 is attached to handle 22 to rotate pinion 20 within recess 66 and thus cause housing 18 to travel along rack 12.

Still referring to FIG. 3, there are shown four bearings 30, 32, 34 and 36 each of which has a generally cylindrical base portion 132, 232, 332 and 432 and a generally rectangular projection 134, 234, 334 and 434 and an outer circumferential surface 136, 236, 336 and 436. The cross-section of cylindrical bases 132, 232, 332 and 432 is circular in the preferred embodiment but it could be any convenient curvilinear shape like an oval. It could even have an irregular curved surface such that the outer circumference could be fluted or even shaped like gear teeth.

Each of bearings 30, 32, 34 and 36 has a load bearing surface 137, 237, 337 and 437 slot facing surface 139, 239, 339 and 439 and load bearing side surface 138, 238, 338 and 438. Load bearing surfaces 138, 238, 338 and 438 are meant to indicate either the left or right side of projections 134, 234, 334 and 434 respectively because each can be load bearing depending upon the applied load.

Projections 134, 234, 334, and 434 are preferably centered on bases 132, 232, 332 and 432, but this need not be the case. The transverse dimension of projections 134, 234, 334 and 434 depends at least in part, on the material from which bearings 30, 32, 34 and 36 are made. Bearings 30, 32, 34 and 36 are preferably made of a high strength, rigid plastic or bronze or some other nonabrading, wearable material. Hardened steel like, for example, AISI 440 C can be used for the bearings and AISI 416 can be used for rack 12.

Careful matching of the bearing and rack material can also permit a variety of other materials to be used.

Still referring to FIG. 3, housing base 52 includes one recess 72 for each bearing 30 and 32 which has a shape conforming to the shape of base portions 132 and 232 so that those base portions may be loosely received in recesses 72. In the preferred embodiment, each recess 72 is a right circular cylinder to accommodate the right circular cylinder shape of base portions 132 and 232, however, recesses 72 could be oval or any other shape necessary to accommodate the variety of shapes possible for bearings 30 and 32. For example, if the outer circumferential surfaces 136 and 236 of bearings 30 and 32 were fluted then the circumferential walls 74 of recesses 72 would be correspondingly fluted.

Housing cover 54 also has recesses 72 which similarly receive bearings 34 and 36.

When the four bearings 30, 32, 34 and 36 which are used in the preferred embodiment are assembled, one recess in housing base 52 receives bearing 30 and one receives bearing 32 and projections 134 and 234 from the bearings 30 and 32 extend into slot 48 in the confronting surface of rack 12. Correspondingly, projections 334 and 434 of bearings 34 and 36 in recesses 72 of housing cover 54 project into slot 50 on the other side of rack 12.

Bearings 30 and 32 on side 44 of rack 12 are spaced longitudinally along slot 48. Bearings 34 and 36 on side 46 of rack 12 are also spaced longitudinally along rack 12. During the assembly of the preferred embodiment of housing 18 bearings 30 and 32 are inserted in recesses 72 of housing base 52 and rack 12 is placed in channel 62. Bearings 34 and 36 are also placed in recesses 72 of housing cover 54 and housing cover 54 is placed over channel 62 and against flange 64. Bolts 56 are inserted through bores 58 into tapped holes 60 and tightened to hold housing cover onto housing base. Pinion 20 is engaged in teeth 40 of rack 12.

The operation of bearings 30, 32, 34 and 36 within housing 18 will now be explained.

When retractor 10 is properly placed in its location above or on the patient and retractor blades 24 are placed into the wound, handle 22 is rotated to move pinion 22 along rack 12 to separate arms 14 and 16. The forces experienced by arm 16 in use create a moment causing housing 18 to rotate with respect to rack 12. Load bearing side surface 138, 238, 338 and 438 of projections 134, 234, 334 and 434 extends into slots 48 and 50 to inhibit this rotation. Both the left and right sides of projections 134, 234, 334 and 434 can be load bearing surfaces and reference characters 138, 238, 338 and 438 are meant to refer to either or both sides. Each bearing 30, 32, 34 and 36 is free to rotate and translate up and down in its recess 72. The use of two bearings spaced longitudinally along rack 12 cause the outer circumferential surfaces 136, 236, 336 and 436 of bearings 30, 32, 34 and 36 to bear against the circumferential surfaces 74 of recesses 72 and inhibit the rotation of housing 18 with respect to rack 12 to avoid contact between the confronting surfaces of rack 12 and housing 18.

At the same time load bearing side surfaces 138, 238, 338 and 438 of bearings 30, 32, 34 and 36 engage the confronting side surfaces 49 or 51 of their corresponding slot 48 or 50 in rack 12 to distribute the load experienced by second arm 16 along surfaces 49 and 51 of slots 48 and 50. Reference characters 49 and 51 are meant to indicate either side of slot 48 and 50 respectively because either can be load bearing depending upon the applied load. Load bearing side surfaces 138, 238, 338 and 438 of projections 134, 234, 334 and 434 provide a relatively large contact surface area on sides 49 and 51 of slots 48 and 50. Thus, even though forces may be reasonably high, the surface area used to distribute these forces is also relatively large so that the stresses will be within acceptable levels.

The foregoing description has been of the preferred embodiment of this invention. A large variety of variations of bearing shapes and numbers and slot shapes and numbers and placement may be used without departing from the spirit of this invention. An alternative embodiment in which rack 12 had projections and bearings had slots to receive those projections would perform satisfactorily.

Instead of using four bearings 30, 32, 34 and 36 as in the embodiment shown in FIGS. 2 and 3, it is possible to use only two bearings. These two bearings could be placed on one side of rack 12 and spaced longitudinally along rack 12 and housing cover 54 could be made of a nonabrading, wearable material like plastic.

Alternatively, one bearing on side 44 of rack 12 and another bearing could be placed on side 46 of rack 12. As long as these two bearings were spaced longitudinally along rack 12 they would still provide the desired force distribution. Since only two bearings instead of four would be used in this alternative embodiment the amount of area to distribute the force would be lower than in the preferred embodiment which uses four bearings.

In a further alternative, three bearings may be used with one bearing on one side of rack 12 and two bearings on the other side of rack 12.

In a further alternative embodiment the bearings could have two spaced apart projections 134 projecting from base 132. These two projections would be accommodated in two corresponding slots in rack 12.

It would also be possible to place two bearings 30 on side 44 of rack 12 and no bearings on side 46 of rack 12 and still accomplish the purpose of the present invention.

In a still further alternative embodiment, it would be possible to accomplish the purpose of this invention with bearings in which the surrounding circumferential surfaces 136, 236, 336 and 436 were fluted or cogged or shaped and the corresponding circumferential surface 74 of recess 72 were similarly fluted or cogged or shaped. If this alternative bearing were loosely placed in its corresponding recess 72 the cogs or flutes or shapes would have many surfaces to contact to increase the area on which the forces could be distributed.

Referring again to FIG. 2 it can be seen that bearings 30 and 34 are placed so as to eliminate contact between housing 18 and rack 12. Load bearing surfaces 137 and 337 of base 132 and 332 directly contact side 44 or 46 of rack 12. Circumferential surfaces 136, 236, 336 and 436 of bearings 30, 32, 34 and 36 contact circumferential surfaces 74 of recesses 72. Load bearing surfaces 138, 238, 338 and 438 on both sides of projections 134, 234, 334 and 434 contact diametrically opposed side surfaces 49 and 51 of slots 48 and 50.

Housing 18 need not be shaped as shown in FIGS. 2 and 3. The same outer shape may be obtained by designing housing 18 as a two pronged yoke extending from arm 16 with the base of the yoke forming a channel to receive rack 12 and one branch of the yoke having a recess for the pinion 20 and each branch of the yoke having recesses 72 for receiving bearings 30. The open side of the yoke can be closed by a convenient cover.

The present invention has been described in conjunction with the preferred embodiment and certain alternative embodiments. Those skilled in the art will appreciate that many modifications and changes may be made in the preferred embodiment without departing from the present invention. It is, therefore, not intended to limit the invention except to set forth in the attached claims.

We claim:
1. In a rack and pinion type retractor having:
a rack having teeth to accept and cooperate with a pinion;
a pinion;
a first arm attached to and extending to one side of said rack;
a second arm extending to the same side of said rack; housing means to limit the rotation of said housing receiving said rack and supporting said pinion;
said rack and pinion operating to separate said arms and retract tissue:
the improvement comprising:
means operatively connected to said rack and said housing means, to limit the rotation of said housing means with respect to said rack when said arms are moved apart to retract tissue to reduce the resulting contact stresses between the rack and the housing means including:
at least two force distributing means mounted on said housing means and including at least three bearings each having a generally cylindrical base and a generally rectangular portion projecting from said base;
with two of said bearings disposed on one side of said rack with one of said bearings disposed on the opposite side of said rack;
said housing means having generally cylindrical recessess therein to receive, in loose fitting rotatable relationship, each of said bearings respectively with the bearings on the same side of said rack spaced longitudinally along said rack;
said rack having a slot on opposed sides thereof aligned with said recesses to receive said rectangular portions from the bearings.
2. The retractor of claim 1 wherein said force distribution means includes at least four bearings having a generally cylindrical base and a generally rectangular portion projecting from a base;
with two of said bearings disposed on each side of said rack;
said housing means having generally cylindrical recesses therein to receive, in loose fitting rotational relationship, each of said bearings respectively with the bearings on the same side of said rack spaced longitudinally along said rack;

said rack having a slot on opposed sides thereof aligned with said recesses to receive said rectangular portions from the bearings.

3. The retractor of claim 1 wherein said housing means includes:
   a housing base for receiving said rack and covering one side of said rack; and,
   a housing cover affixed to said housing base and covering the opposed side of said rack.

4. The retractor of claim 1 wherein said force distributing means are made of a substantially nonabrading wearing material.

5. The retractor of claim 1 wherein said force distributing means are made of plastic.

6. The retractor of claim 1 wherein said force distributing means are made of hardened steel.

7. The retractor of claim 1 wherein said force distributing means are made of bronze.

* * * * *

UNITED STATES PATENT AND TRADEMARK OFFICE
CERTIFICATE OF CORRECTION

PATENT NO. : 5,067,477

DATED : November 26, 1991

INVENTOR(S) : John Santangelo

It is certified that error appears in the above-identified patent and that said Letters Patent is hereby corrected as shown below:

Claim 1, column 6, line 31, "to limit the rotation of said housing" should be -- connected to said second arm for --; and Claim 2, column 6, line 59, after "bearings", insert -- each --.

Signed and Sealed this

Twenty-first Day of September, 1993

Attest:

BRUCE LEHMAN

*Attesting Officer*     *Commissioner of Patents and Trademarks*